United States Patent [19]
Ertel et al.

[11] Patent Number: 5,182,523
[45] Date of Patent: Jan. 26, 1993

[54] APPARATUS FOR ASCERTAINING THE ALCOHOL CONTENT OR CALORIFIC VALUE OF A MIXTURE BY CAPACITANCE MEASUREMENT

[75] Inventors: Gernot Ertel, Bischberg, Fed. Rep. of Germany; Ludwig Brabetz, Tournefeuille, France; Waldemar Schwarz, Schwarzenbruck, Fed. Rep. of Germany

[73] Assignee: Siemens Aktiengesellschaft, Munich, Fed. Rep. of Germany

[21] Appl. No.: 753,206

[22] Filed: Aug. 30, 1991

[30] Foreign Application Priority Data
Aug. 30, 1990 [FR] France ............... 90 116687

[51] Int. Cl.⁵ .................... G01R 27/26; G01N 27/22
[52] U.S. Cl. .................... 324/663; 324/690; 73/61.4
[58] Field of Search ............... 324/446, 448, 450, 658, 324/660, 663, 664, 685, 686, 689, 690; 73/61 R, 61.1 R, 61.41, 61.43

[56] References Cited
U.S. PATENT DOCUMENTS

| | | | |
|---|---|---|---|
| 4,887,023 | 12/1989 | Gimson | 324/664 |
| 4,939,467 | 7/1990 | Noglami et al. | 324/663 |
| 4,939,468 | 7/1990 | Takeuchi | 324/690 |

FOREIGN PATENT DOCUMENTS

| | | |
|---|---|---|
| 0380751 | 8/1990 | European Pat. Off. |
| 3923992 | 1/1990 | Fed. Rep. of Germany |
| 56-104243 | 8/1981 | Japan |
| 0057253 | 4/1982 | Japan ............... 73/61.1 R |

Primary Examiner—Gerard R. Strecker
Assistant Examiner—Diep Do
Attorney, Agent, or Firm—Herbert L. Lerner; Laurence A. Greenberg

[57] ABSTRACT

An apparatus for ascertaining the alcohol content or the calorific value of a mixture containing alcohol and gasoline includes an electrically conductive housing through which the mixture flows and in which at least one physical parameter of the mixture is measured to produce a measurement. An electronic measuring circuit is disposed in the housing for evaluating the measurement. The housing has a wall with a part of the wall forming a first electrode of a capacitor. An intermediate plate is associated with the housing. An electrically conductive sensor element is secured in the intermediate plate and partly surrounded by the mixture. The electrically conductive sensor element forms a second electrode of the capacitor and forms an electrical connection between the second electrode and the measuring circuit.

9 Claims, 2 Drawing Sheets

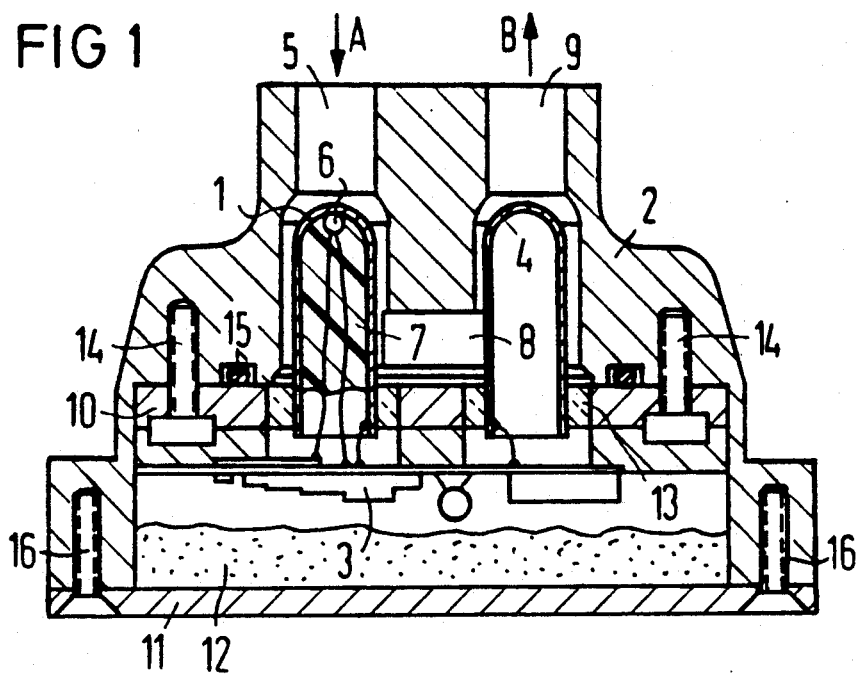
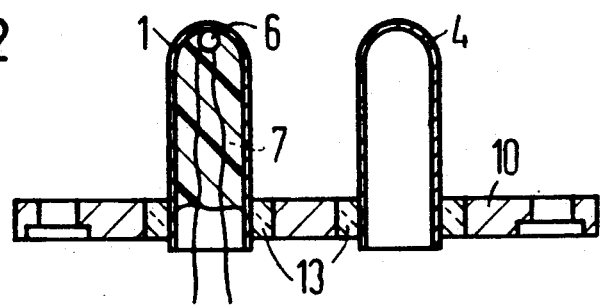
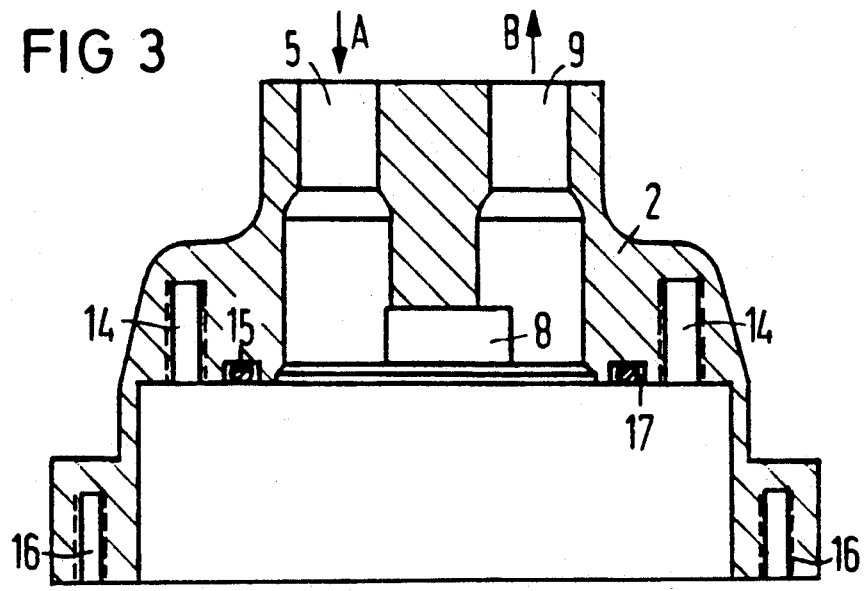

APPARATUS FOR ASCERTAINING THE ALCOHOL CONTENT OR CALORIFIC VALUE OF A MIXTURE BY CAPACITANCE MEASUREMENT

The invention relates to an apparatus for ascertaining the alcohol content or the calorific value of a mixture containing alcohol and gasoline, by measuring at least one physical parameter of the mixture in an electrically conductive housing through which the mixture flows and by evaluating the measurement in an electronic measuring circuit that is disposed in the housing, wherein part of the wall of the housing forms a first electrode and an electrically conductive sensor element forms a second electrode of a capacitor.

Both economic and ecological goals and the need for a safe fuel supply have triggered an extensive search for alternative fuels. Since petroleum resources are limited, a search is on for other alternative forms of energy. One alternative has proved to be alcohol, which can be produced from non-fossil energy resources. Since conventional fuels such as gasoline, which are produced from petroleum, are widely used, the possibility should exist of admixing arbitrary proportions of alcohol with the gasoline in fuel-injected internal combustion engines. In order to achieve satisfactory operation of such an engine, the alcohol content, in other words the proportion of alcohol in the mixture by volume, must be known. In order to enable injecting an appropriate quantity of fuel into the combustion chamber for a given operating state, the alcohol content must be determined on a continuous basis.

German Published, Non-Prosecuted Application DE 38 41 318 A, corresponding to Published European Application 0 380 751 A1, describes an apparatus for ascertaining the alcohol content and calorific value of a mixture by measuring physical parameters of the mixture in a housing. The apparatus has an electronic measuring circuit. A middle cylinder and part of the wall of a housing form the electrodes of a capacitor. The middle cylinder is kept completely within the mixture by centering disks. The measuring circuit is located in the interior of the middle cylinder. A voltage supply lead and a signal output to and from the measuring circuit extend through the centering disks.

The centering disks, acting as an electrical connection from the middle cylinder to the housing, lead through the space through which the mixture flows. Since the mixture is pumped by a fuel pump at high pressure in a fuel-injected engine, pulsating pumping of the mixture can cause axial and radial vibrations, which make the apparatus unstable. The voltage lead and the signal output extending through the centering disks are therefore likewise vulnerable to mechanical influences, such as pressure strain. Moreover, a relatively major production effort and expense must be undertaken in order to center the middle cylinder in the housing.

It is accordingly an object of the invention to provide an apparatus for ascertaining the alcohol content or calorific value of a mixture, which overcomes the hereinafore-mentioned disadvantages of the heretofore-known devices of this general type and which is vibration-proof and pressure-proof.

With the foregoing and other objects in view there is provided, in accordance with the invention, an apparatus for ascertaining the alcohol content or the calorific value of a mixture containing alcohol and gasoline, comprising an electrically conductive housing through which the mixture flows and in which at least one physical parameter of the mixture is measured to produce a measurement, an electronic measuring circuit disposed in the housing for evaluating the measurement, the housing having a wall with a part of the wall forming a first electrode of a capacitor, an intermediate plate associated with the housing, and an electrically conductive sensor element being secured in the intermediate plate and partly surrounded by the mixture, the electrically conductive sensor element forming a second electrode of the capacitor and forming an electrical connection between the second electrode and the measuring circuit.

In accordance with another feature of the invention, the housing has a portion in which the measuring circuit is disposed and a remaining portion, and the intermediate plate hermetically seals off the remaining portion of the housing from the measuring circuit.

In accordance with a further feature of the invention, the sensor element is hermetically glassified into the intermediate plate.

In accordance with an added feature of the invention, the sensor element has a surface, and the sensor element is spaced apart from the wall of the housing by substantially the same distance over all of the surface of the sensor element.

In accordance with an additional feature of the invention, the sensor element is tubular and has a wall with a thickness being at most equal to 1.5 mm.

In accordance with yet another feature of the invention, the housing has a given space through which the mixture flows, and the measuring circuit is disposed on the intermediate plate outside the given space.

In accordance with yet a further feature of the invention, there is provided a temperature sensor being disposed in the sensor element and being in thermal contact with the wall of the sensor element.

In accordance with yet an added feature of the invention, there is provided another sensor element secured in the intermediate plate.

In accordance with yet an additional feature of the invention, the housing has a fuel conduit disposed therein between the sensor elements, the fuel conduit having an incline, bevel or slant for setting the mixture flowing therethrough into rotation.

In accordance with again another feature of the invention, the housing and the intermediate plate are made of aluminum and are coated with copper and nickel.

In accordance with a concomitant feature of the invention, at least one of the sensor elements is made from an iron-nickel alloy.

The advantages of the invention are, among others, that the measuring circuit is protected against external influences, in particular those of an electromagnetic, mechanical and thermal nature, and that its structural size is small and its production cost is low. The glassification or vitrification of a sensor element in an intermediate plate also has an advantageous effect, since the sensor element is thereby insulated from the housing, and this structure is completely vibration-proof, pressure-proof, temperature-stable and fuel-resistant. This makes other sealing devices which are physically and chemically unstable, unnecessary. The glassification of the sensor element has the further advantage of attaining an electrical connection with an electronic measuring circuit over the shortest path, with high mechanical strength, by means of the electrically conductive wall of the sensor element.

Other features which are considered as characteristic for the invention are set forth in the appended claims.

Although the invention is illustrated and described herein as embodied in an apparatus for ascertaining the alcohol content or calorific value of a mixture, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 1 is a diagrammatic, cross-sectional view of an apparatus according to the invention;

FIG. 2 is a cross-sectional view of two sensor elements that are glassified in an intermediate plate of the apparatus of FIG. 1;

FIG. 3 is a cross-sectional view of a housing of the apparatus of FIG. 1;

Figure 4:
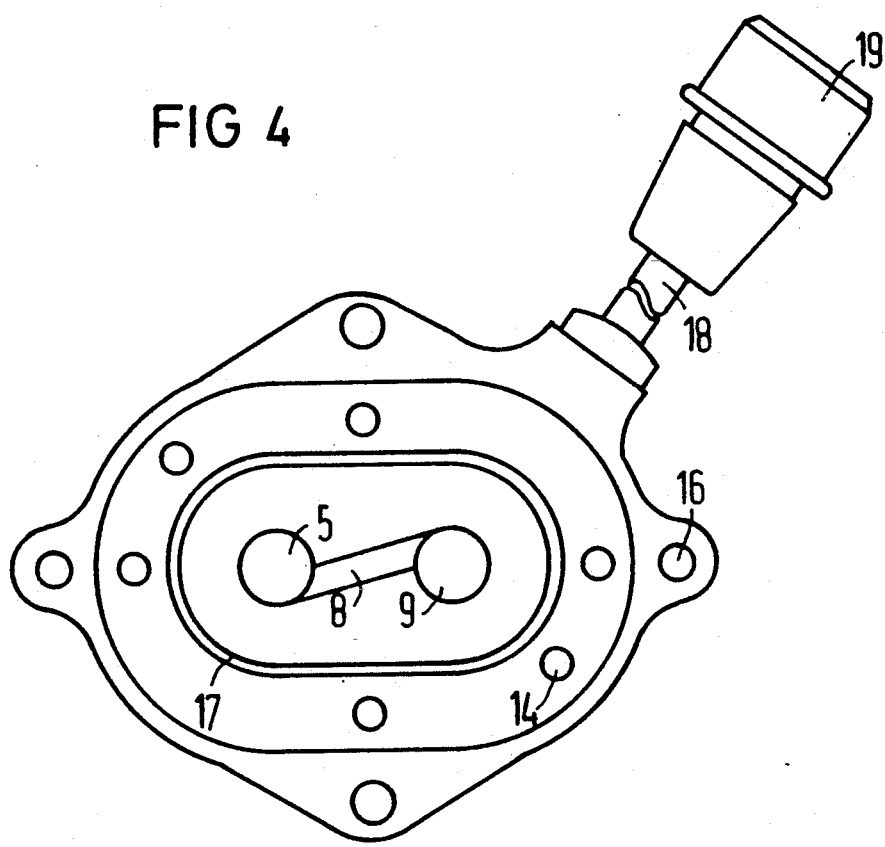
FIG. 4 is a bottom plan view of the housing of FIG. 3.

Before discussing the drawings in detail, it is noted that in order to measure the alcohol content or the calorific value of a mixture containing alcohol and gasoline in arbitrary proportions, at least one physical parameter of the mixture must be measured in an apparatus. By measuring capacitance C and relative dielectric constant $\epsilon_r$ resulting therefrom, the alcohol content can be ascertained, for instance in the form of the proportion of alcohol by volume in the mixture.

The dielectric constant $\epsilon_r$ of the mixture depends on the proportions by volume and on the respective dielectric constants of alcohol and gasoline. The relative dielectric constant of gasoline is approximately 2.05 to 2.15, and that of alcohol, in this case methanol, is approximately 32.

Referring now to the figures of the drawing in detail and first, particularly, to FIG. 1 thereof, it is seen that the dielectric constant $\epsilon_r$ is determined by measuring the capacitance C of a capacitor, which is constructed as a first sensor element 1 and part of a wall of a housing 2 and which is filled with a mixture as a dielectric, and by a reference capacitance, in accordance with a formula:

$$\epsilon_r = C/C_0.$$

This reference capacitance $C_0$ is determined beforehand by using the same capacitor, but without the dielectric, that is in a vacuum. It is stored as a constant in an electronic measuring circuit 3 and it amounts to approximately 3 to 5 pF and also takes existing parasitic capacitances into account.

In order to attain full compensation for secondary effects, such as the frequency dependency of the capacitance C and the temperature dependency of the dielectric constant $\epsilon_r$, when the alcohol content in a mixture is ascertained, the following three physical parameters must be measured: the capacitance C, a conductance value G between a sensor element and part of the wall of the housing 2 located facing the sensor element, and the temperature T of the mixture.

The capacitance C is measured between the first sensor element and the facing portion of the housing 2, through which the mixture flows. The measurement of the capacitance C is distorted by water in the mixture or other contaminants or cross influences. These cross influences on the capacitance C from contamination of the mixture can be corrected by knowledge of the conductance G, for instance by calculation or by using a table stored in a microcontroller. The conductance G is determined between a second, identically constructed sensor element 4 and a further part of the wall of the housing 2 that faces the sensor element.

During operation, the mixture flows through a fuel inlet 5, in a flow direction represented by arrows A and B of FIG. 1, to the first sensor element 1, in which a temperature sensor 6 is mounted. This temperature sensor 6, which is constructed as an NTC resistor, is coated with thermally conductive paste and inserted into the tip of the first sensor element 1. A plastic body 7 keeps the temperature sensor 6 in position. Electric supply lines to the temperature sensor 6 lead directly to the measuring circuit 3.

The temperature sensor 6 is thus in thermal contact with the wall of the sensor element 1, the temperature of which is determined by the mixture flowing past. At a given mixture ratio of gasoline and alcohol, the dielectric constant $\epsilon_r$ is first measured as a function of the temperature T and stored in the form of a performance graph in a memory element, such as a ROM, of the measuring circuit 3.

The mixture flows from the first sensor element 1, through a fuel conduit 8 with an incline, bevel or slant, to the second sensor element 4, and finally reaches a fuel outlet 9, which is located upstream of the injection location in the engine chamber.

The housing 2 is shaped in such a way that the spacing between one of the sensor elements 1 or 4 and the housing is substantially equal. The tip of one of the sensor elements 1 or 4 protruding into the mixture is shaped in such a way that on one hand, the pressure drop is less than 0.1 bar for a flow rate of 3 liters per minute, and on the other hand, the mixture is made turbulent. Air bubbles that form on the wall of one of the sensor elements 1 or 4 or of the housing 2 as a result of the low evaporation temperature of the mixture, which is approximately 80° C., can thus be floated out, so that they do not distort the measurement of the dielectric constant $\epsilon_r$.

The two sensor elements 1 and 4 are glassified or vitrified in an intermediate plate 10 (see FIG. 2 as well), which hermetically seals off the space filled with the mixture from the measuring circuit 3. A glassification 13 is pressure-proof up to 70 bar.

The measuring circuit 3 is cooled through the intermediate plate 10 since, as a rule, the temperature of the mixture flowing in from the fuel tank is cooler than the temperature in the engine chamber.

The measuring circuit is located on the lower surface of the intermediate plate 10, outside the space through which the mixture flows. It includes an analog part, in which the physical parameters are converted into corresponding electrical signals, and a digital part, in which the measured data are evaluated by a microcontroller and the calculated alcohol content is passed on to an engine control system.

Within one measuring cycle, the capacitance C and the conductance G of the measuring configuration are ascertained with the mixture as the dielectric, and the temperature T of the mixture is determined. The alcohol content is ascertained from these. One measuring cycle lasts about 100 ms, at a clock frequency of the measuring circuit 3 of about 10 MHz. The alcohol content is reported, either in the form of an analog voltage or digitally as a modulated signal, to the engine control system, for controlling the injection quantity.

The lower surface of the housing 2 is closed off by a metal base plate 11. This accordingly acts as an external protection for the electronic measuring circuit 3. In particular, the measuring circuit 3 is thus shielded from electromagnetic fields. A layer 12 of silicon additionally seals off the measuring circuit 3 and protects it from oxidizing.

The sheath-like sensor elements 1, 4 shown in FIG. 2 are glassified into the intermediate plate 10. The sensor elements 1, 4 are made in a material-saving manner in the form of deep-drawn parts from a nickel-iron alloy, which in this case is NiFe V540. This material has the advantage of easily establishing electrical contact with a wire to the measuring circuit 3. One wire is welded to each sensor element 1 and 4 and soldered in the measuring circuit 3. The sensor elements 1 and 4 thus respectively act as an electrode of the capacitor and as an electrical connection between the electrode and the measuring circuit 3. Since the wall thickness is so slight, approximately 1 mm, that good heat transfer takes place from the mixture to the temperature sensor 6 through the wall of the sensor element 1.

The cylindrically constructed sensor elements 1, 4 are held centrally in a bore in the intermediate plate 10 by the glassification 13. The glass insulates the sensor elements 1, 4 from the intermediate plate. Glass is not only vibration-proof and extremely pressure-proof, but it is also resistant to the mixture and is temperature-stable in the specified temperature range of from −40° C. to +125° C. Due to the glassification, the sensor elements 1, 4 are accurately positioned in terms of their location. This facilitates assembly and mounting of the apparatus.

The spacing between the sensor element 1 or 4 and the intermediate plate 10 is the same in every apparatus. This makes for electrical reproducibility. The capacitance between the sensor element 1 and the intermediate plate 10 enters into the determination of the dielectric constant $\epsilon_r$ in the form of parasitic capacitance.

Just like the housing 2, the intermediate plate 10 is made from aluminum by pressure casting. Although aluminum is light in weight and economical, it is not resistant to the chemically aggressive mixture. It is therefore coated with copper and nickel. Other materials with good electrical conductivity that are resistant to the mixture may also be used. A plastic equipped with a metallization that acts as an electrode can also be used as a material for the housing.

FIG. 3 shows a cross section through the housing 2 of the apparatus. The mixture flows through the housing 2 in the directions indicated by the arrows A, B. The fuel conduit 8 connects the fuel inlet 5 to the fuel outlet 9. The fuel inlet 5 and the fuel outlet 9 each have a non-illustrated thread, with the aid of which fuel lines leading from the fuel tank and to an injection location are respectively screwed on.

Fastening bores 14 in the housing 2 are provided with threads for securing the intermediate plate 10 to the housing. In order to additionally seal off the housing 2 from the measuring circuit 3, an 0-ring 15 is fitted in between the housing and the intermediate plate 10.

Other fastening bores 16, which are provided with threads, are located in the lower part of the housing 2. The base plate 11 is thereby secured to the housing 2, and the entire apparatus is thus sealed off. The housing 2 is a good electrical conductor and thus shields against electromagnetic fields. It is also protected against moisture.

The fuel conduit 8 shown in FIG. 4 extends obliquely between the fuel inlet 5 and the fuel outlet 9. This sets the mixture flowing past the second sensor element 4 into rotation. Thus even at moderate flow rates, air bubbles that may form on the wall of the second sensor element 4 or of the housing 2 are floated away.

When the apparatus is assembled, the 0-ring 15 is placed in a groove 17 as a sealing ring. The intermediate plate 10 is then screwed onto the inner part of the housing 2, and the base plate 11 is screwed onto the outer part of the housing. The fastening screws used in the bores 14, 16 for this purpose can be seen in FIG. 4.

Disposed on the outer rim of the housing 2 are four flanges having the bores 16 by means of which the base plate 11 is secured to the housing 2. The apparatus is electrically connected to an engine control system through a connection cable 18 with a plug 19.

Figure 5:
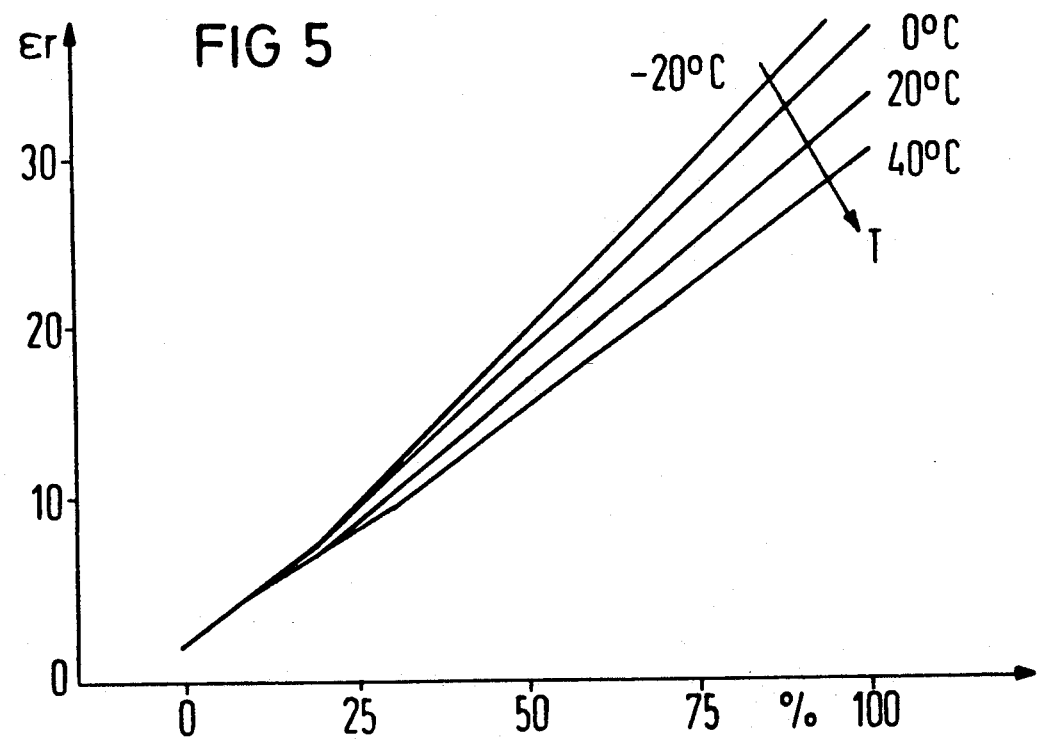
FIG. 5 is a performance graph of the relative dielectric constant $\epsilon_r$ of the mixture, which is plotted as a function of the alcohol content and temperature T.

The performance graph shown in FIG. 5 illustrates the dependency of the relative dielectric constant $\epsilon_r$ of the mixture on the alcohol content and on the temperature T of the mixture.

In order to determine the alcohol content of the mixture, the capacitance C between the sensor element and part of the wall of the housing 2 is first determined, with the aid of that sensor element 1. Parallel to the measurement of C, the temperature T of the mixture is measured with the temperature sensor 6. Parallel to this, the conductance G is determined with the aid of the second sensor element 4. Then, the relative dielectric constant is calculated from the measured capacitance C, which is corrected with the aid of the conductance G, and from the memorized reference capacitance $C_0$.

The alcohol content can then be ascertained with the aid of the performance graph from the dielectric constant $\epsilon_r$ and the temperature T. In FIG. 5, the alcohol content (in %) of the total volume of the mixture is plotted on the X axis, and the dielectric constant $\epsilon_r$ is plotted on the Y axis.

With this apparatus, it is possible to measure the alcohol content in the mixture in proportions of 0% to 100% by volume. The measurement error remains below 5%.

Since gasoline and alcohol have different calorific values, the calorific value of the mixture can be determined by way of the alcohol content. The calorific value of gasoline is approximately 32 MJ per liter, and that of methanol is approximately 15.6 MJ per liter.

In some applications, it is more favorable to provide the apparatus according to the invention for ascertaining the alcohol content with only one sensor element. In that case, a capacitance C and a conductance G are measured in chronological succession.

In a third exemplary embodiment, a fuel inlet and a fuel outlet are horizontally constructed. The mixture then flows through the tip of a sensor element. If a second sensor element is also present, then the mixture flows through a fuel conduit and then through the tip of the second sensor element. The location of the sensor elements is the same as in the first exemplary embodiment.

In all three exemplary embodiments, the temperature sensor for measuring the temperature T is disposed in whichever sensor element also measures the capacitance C.

We claim:

1. An apparatus for ascertaining the alcohol content or the calorific value of a fuel containing a mixture of alcohol and gasoline, comprising:
    an electrically conductive housing having inside walls;
    a removable plate disposed in said housing, said plate having a fuel side and an exterior side;
    said inside walls of said housing and said fuel side of said plate defining a fuel conduit in said housing;
    an electronic measuring circuit disposed in said housing apart from said fuel conduit;
    an electrically conductive sensor element extending from said plate into said fuel conduit, said sensor element being secured in said plate in an electrically insulated and hermetically sealed manner;
    wherein a part of said inside walls forms a first electrode and said sensor element forms a second electrode, said electrodes having a fixed geometric relationship with respect to one another to form a capacitor and being electrically connected with said measuring circuit, the fuel in said fuel conduit serving as a dielectric of said capacitor.

2. The apparatus according to claim 1 wherein said sensor element is hermetically secured in said plate by means of glass.

3. The apparatus according to claim 1, wherein said sensor element is tubular and has a wall with a thickness being at most equal to 1.5 m.

4. The apparatus according to claim 3, wherein said measuring circuit is disposed on said exterior side of said plate.

5. The apparatus according to claim 4, including a temperature sensor being disposed in said sensor element and being in thermal contact with said wall of said sensor element.

6. The apparatus according to claim 5, wherein said sensor element is a first sensor element, and including a second sensor element secured in said plate parallel to said first sensor element and extending into said fuel conduit to be surrounded by the fuel, said first sensor element being a means for measuring a first physical parameter of the fuel and said second sensor element being a means for measuring a second physical parameter of the fuel.

7. The apparatus according to claim 6, wherein said housing has a fuel connecting conduit disposed therein between said sensor element, said fuel connecting conduit having an incline for setting the fuel flowing therethrough into rotation.

8. The apparatus according to claim 7, wherein said housing and said plate are made of aluminum and are coated with copper and nickel.

9. The apparatus according to claim 8, wherein at least one of said sensor elements is made from an iron-nickel alloy.

* * * * *